United States Patent
Yamamoto et al.

(10) Patent No.: US 9,482,747 B2
(45) Date of Patent: Nov. 1, 2016

(54) MOBILE ULTRASONIC DIAGNOSTIC DEVICE

(71) Applicant: HITACHI ALOKA MEDICAL, LTD., Mitaka-shi, Tokyo (JP)

(72) Inventors: Masa Yamamoto, Mitaka (JP); Keigo Ninomiya, Mitaka (JP)

(73) Assignee: HITACHI, LTD., Tokyo (JP)

(*) Notice: Subject to any disclaimer, the term of this patent is extended or adjusted under 35 U.S.C. 154(b) by 168 days.

(21) Appl. No.: 14/369,989

(22) PCT Filed: Dec. 7, 2012

(86) PCT No.: PCT/JP2012/081843
§ 371 (c)(1),
(2) Date: Jun. 30, 2014

(87) PCT Pub. No.: WO2013/118382
PCT Pub. Date: Aug. 15, 2013

(65) Prior Publication Data
US 2014/0334263 A1 Nov. 13, 2014

(30) Foreign Application Priority Data
Feb. 6, 2012 (JP) ................................. 2012-022877

(51) Int. Cl.
*G01S 7/52* (2006.01)
*A61B 8/00* (2006.01)
*A61B 8/14* (2006.01)

(52) U.S. Cl.
CPC ............... *G01S 7/52* (2013.01); *A61B 8/4427* (2013.01); *A61B 8/54* (2013.01); *A61B 8/56* (2013.01); *A61B 8/14* (2013.01)

(58) Field of Classification Search
CPC ........ A61B 8/4427; A61B 8/56; A61B 8/54; A61B 8/14; G01S 7/52
See application file for complete search history.

(56) References Cited

U.S. PATENT DOCUMENTS 6,527,721 B1    3/2003  Wittrock et al.
7,652,259 B2*   1/2010  Kimchy .................. A61B 1/05
                                              250/370.08
(Continued)

FOREIGN PATENT DOCUMENTS

CN    1504858 A    6/2004
CN    2673405 Y    1/2005
(Continued)

OTHER PUBLICATIONS

Translation of JP200934305.*
(Continued)

*Primary Examiner* — Daniel Pihulic
(74) *Attorney, Agent, or Firm* — Westerman, Hattori, Daniels & Adrian, LLP

(57) ABSTRACT

A mobile ultrasonic diagnostic device comprising: a battery; an adapter connection detection unit that detects the connection status of an AC adapter that supplies power to each constituent element of the device; and a processing determination unit (determination unit) that determines the processing for each constituent element on the basis of the connection status of the AC adapter. Each constituent element (a processing unit and constituent elements other than the processing unit) are processed on the basis of the processing determined by the processing determination unit (determination unit), and, as a result, the device can be safely used even if there is a possibility that power cannot be supplied from the battery.

6 Claims, 8 Drawing Sheets

(56) References Cited

U.S. PATENT DOCUMENTS

| | | | |
|---|---|---|---|
| 2006/0206733 A1 | 9/2006 | Ono | |
| 2006/0237652 A1* | 10/2006 | Kimchy | A61B 1/05 250/363.02 |
| 2010/0160786 A1 | 6/2010 | Nordgren et al. | |
| 2014/0334263 A1* | 11/2014 | Yamamoto | A61B 8/4427 367/87 |

FOREIGN PATENT DOCUMENTS

| | | |
|---|---|---|
| CN | 1825250 A | 8/2006 |
| CN | 101873032 A | 10/2010 |
| CN | 201945945 U | 8/2011 |
| CN | 201985577 U | 9/2011 |
| CN | 202059208 U | 11/2011 |
| JP | 2003-187563 A | 7/2003 |
| JP | 2004-508126 A | 3/2004 |
| JP | 2006-236425 A | 9/2006 |
| JP | 2009-34305 A | 2/2009 |
| JP | 2009-273517 A | 11/2009 |
| JP | 2010-528697 A | 8/2010 |
| JP | 2011-108158 A | 6/2011 |
| JP | 5107992 B2 | 12/2012 |
| WO | 2008/146208 A1 | 12/2008 |
| WO | WO 2013118382 A1 * | 8/2013 ........... A61B 8/4427 |

OTHER PUBLICATIONS

Using Advanced Power Options in Windows Vista, https://www.youtube.com/watch?v=fxASUSh4n3U , Nov. 8, 2008.*

Windows Vista Tip—Increase CPU performance, https://www.youtube.com/watch?v=n9aMlyn3YYI , Jul. 2009.*

Reducing Power Consumption (Windows), https://msdn.microsoft.com/en-us/library/ms699540(v=vs.85).aspx/, Feb. 8, 2011.*

International Search Report dated Mar. 12, 2013 issued in corresponding application No. PCT/JP2012/081843.

Office Action dated Jul. 1, 2015, issued in counterpart Chinese Patent Application No. 201280069176.1, with English translation (14 pages).

Notification of Transmittal of Translation of the International Preliminary Report on Patentability (Form PCT/IB/338) of International Application No. PCT/JP2012/081843 mailed Aug. 21, 2014 with Forms PCT/IB/373, PCT/IB/326 and PCT/ISA/237.

Chinese Office Action dated Mar. 16, 2016, issued in counterpart Chinese Patent Application No. 201280069176.1, with English translation (37 pages).

Office Action dated Aug. 16, 2016, issued in counterpart Japanese Patent Application No. 2013-557375, with Partial English translation. (5 pages).

* cited by examiner

MOBILE ULTRASONIC DIAGNOSTIC DEVICE

TECHNICAL FIELD

The present invention relates to a mobile ultrasonic diagnostic device, and particular to a mobile ultrasonic diagnostic device having an advantage of being conveniently installed in a place (ease of installation).

BACKGROUND ART

Although conventional ultrasonic diagnostic devices are mainly of a wagon type in which various devices are mounted on a movable wagon, mobile ultrasonic diagnostic devices having excellent portability are also on the market. For example, the so-called notebook type mobile ultrasonic diagnostic device has a structure in which a lid chassis with a display device is foldable with respect to a thin body chassis.

Design has been implemented to display, on a display unit, an alarm signal generated based on the comparison result between the battery level of a mobile ultrasonic diagnostic device and a threshold (as cited in, for example, Patent Document 1).

CITATION LIST

Patent Document

Patent Document 1: JP 2009-273517 A

SUMMARY OF THE INVENTION

Technical Problem

Although Patent Document 1 describes that the alarm signal is displayed based on the battery level of the mobile ultrasonic diagnostic device, if electrical power cannot be supplied from the battery when processing is being executed in the mobile ultrasonic diagnostic device, the processing being executed is interrupted and cannot be completed. For example, if data are being transferred to outside the mobile ultrasonic diagnostic device, data transfer cannot be completed. In that case, the mobile ultrasonic diagnostic device is shut down.

Therefore, there is a possibility that currently-running processing cannot be continued, and data are lost while they are being transferred.

An object of the present invention is to provide a mobile ultrasonic diagnostic device which can be used safely even if there is a possibility that the battery will not be able to supply electrical power.

Solution to Problem

In order to achieve the object of the present invention, the present invention has a battery, an adaptor connection detection unit which detects a connection state of an AC adapter for supplying electrical power to components, a processing determination unit which determines processing operations of each component based on the connection state of the AC adaptor, and the processing of each components is performed based on the processing operations determined by the processing determination unit.

The present invention also has a processing unit having a component for performing predetermined particular processing, and performs the processing in the component based on the processing operations determined by the processing determination unit.

For example, when the AC adaptor is not connected to an electric outlet, the processing determination unit determines to cause the processing unit to stop the particular processing, and the processing unit stops execution of the particular processing. When the AC adaptor is not connected to the electric outlet, the processing determination unit determines to cause the component other than the processing unit to perform processing other than the particular processing, and the component other than the processing unit executes the processing other than the particular processing.

Advantageous Effects of Invention

The present invention can be used safely even if there is a possibility that a battery will not be able to supply electrical power.

DESCRIPTION OF EMBODIMENT

Figure 1:
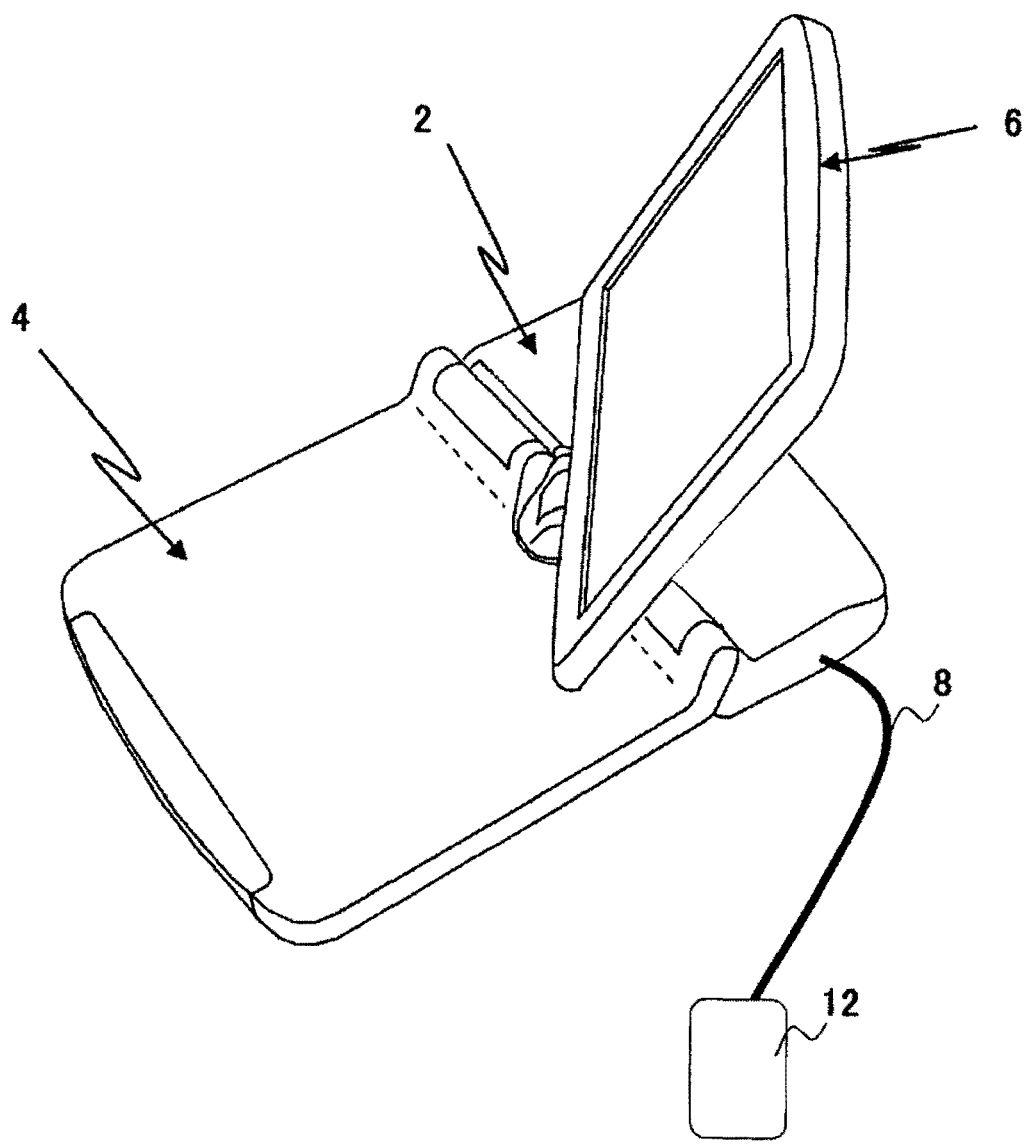
FIG. 1 shows an external view of a mobile ultrasonic diagnostic device according to the present invention.

FIG. 1 shows an external view of the mobile ultrasonic diagnostic device according to the present invention. As shown in FIG. 1, the mobile ultrasonic diagnostic device has, as a structure, a body chassis 2 for storing a device having a main processing function, a keyboard chassis 4 having an operating unit to be operated by an operator, and a display chassis 6 having an image display unit for displaying an image. Further, the body chassis 2 is connected to an ultrasound probe 12 for receiving and transmitting ultrasonic waves, via a cable 8.

Embodiment 1

Figure 2:
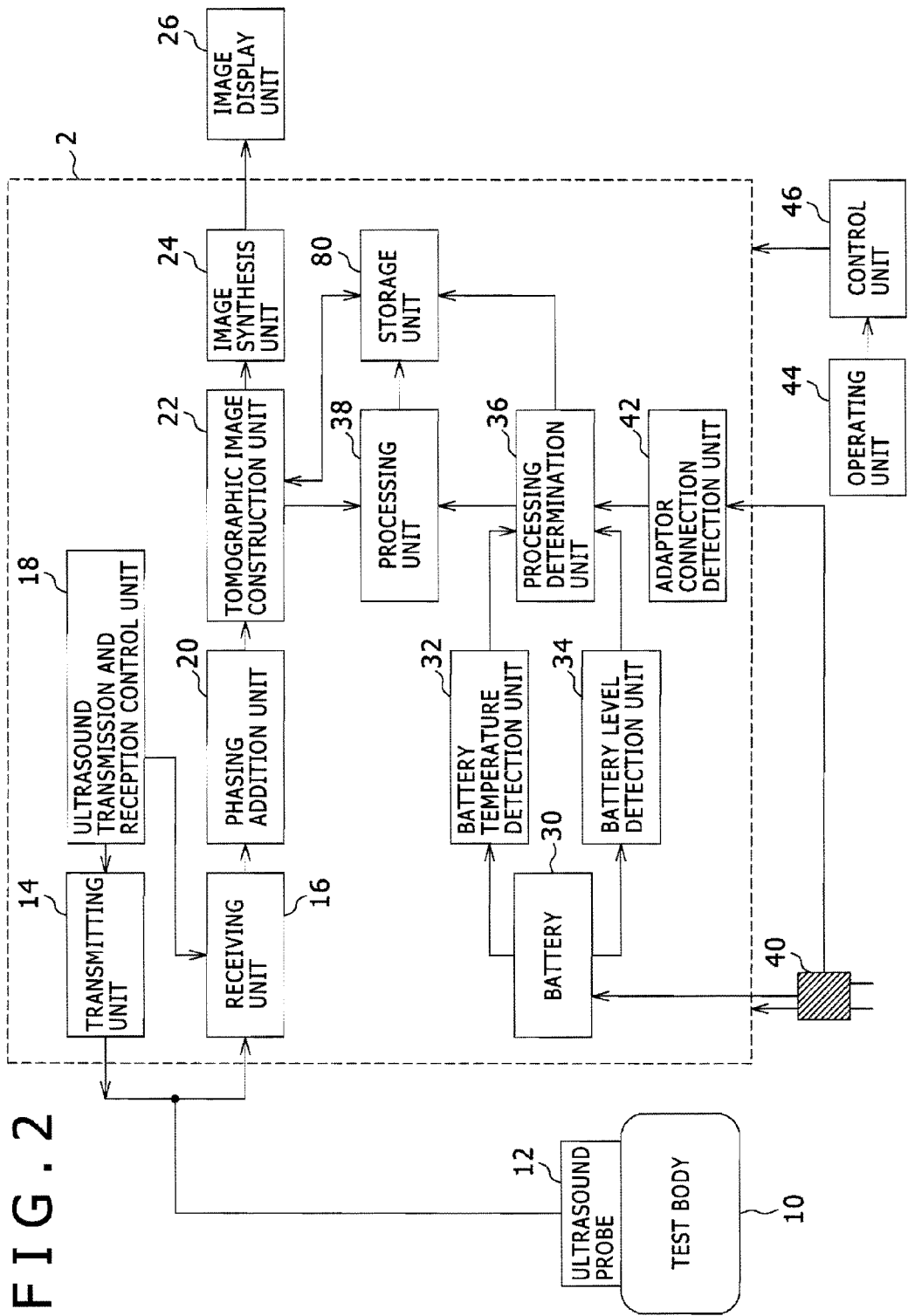
FIG. 2 shows a configuration diagram of the mobile ultrasonic diagnostic device according to the present invention.

FIG. 2 shows a block diagram which illustrates a structure of the mobile ultrasonic diagnostic device. As shown in FIG. 2, the mobile ultrasonic diagnostic device has the ultrasound probe 12 which is placed on a test object 10 for transmitting and receiving ultrasonic waves, a transmitting unit 14 which transmits ultrasonic waves to the test object 10 via the ultrasound probe 12 repeatedly at time intervals, a receiving unit 16 which receives ultrasonic waves reflected from the test object 10 as a reflection echo signal, an ultrasound transmission and reception control unit 18 which controls the transmitting unit 14 and the receiving unit 16, and a phasing addition unit 20 which phases and adds the reflection echo signals based on the ultrasonic waves received by the receiving unit 16.

In addition, the mobile ultrasonic diagnostic device has a tomographic image construction unit 22 which constructs a tomographic image, such as a black and white tomographic image, of the test object 10 based on RF frame data which are generated by phased addition in the phasing addition unit 20, an image synthesis unit 24 which adjusts the tomographic image so as to be displayed on the image display unit 26, superimposes the tomographic image with other images or displays those images parallel to each other to thereby synthesize the images, and an image display unit 26 which displays the image output from the image synthesis unit 24.

Further, the mobile ultrasonic diagnostic device has a battery 30 which supplies electrical power to components, a battery temperature detection unit 32 which detects the temperature of the battery 30, a battery level detection unit 34 which detects the battery level of the battery 30, an AC adaptor 40 which supplies electrical power to the components and charges the battery 30, and an adaptor connection detection unit 42 which detects that the AC adaptor 40 is connected to an electric outlet, and that the AC adaptor 40 supplies electrical power to the components or that the AC adaptor 40 charges the battery 30.

The components are those constituting the mobile ultrasonic diagnostic device and mainly include the numbered elements in FIG. 2 (such as the transmitting unit 14, the receiving unit 16, the ultrasound transmission and reception control unit 18, the phasing addition unit 20, the tomographic image construction unit 22, the image synthesis unit 24, and a processing unit 38).

In addition, the mobile ultrasonic diagnostic device has a processing determination unit 36 which determines a processing method of the processing unit 38 based on a connection state of the AC adaptor 40, and performs processing in the components (the processing unit 38 and the components other than the processing unit 38) based on the processing determined by the processing determination unit 36. Further, the mobile ultrasonic diagnostic device has the processing unit 38 which performs particular processing based on the processing determined by the processing determination unit 36, and a storage unit 80 which stores the determination information of the processing determination unit 36 and the processing information of the processing unit 38 or the components other than the processing unit 38.

Still further, the mobile ultrasonic diagnostic device has an operating unit 44, and a control unit 46 which transfers control information to the components based on an instruction received from the operating unit 44.

Next, the components of the mobile ultrasonic diagnostic device will be further described in detail below. The ultrasound probe 12 is formed by arranging a plurality of vibrators, and has a function of transmitting and receiving ultrasonic waves to/from the test object 10 via the vibrators.

The transmitting unit 14 has a function of generating wave transmission pulses for driving the ultrasound probe 12 and generating ultrasonic waves, and a function of setting the convergence point of the transmitted ultrasonic waves at a certain depth. In addition, the receiving unit 16 amplifies the reflection echo signal which is based on ultrasonic waves received by the ultrasound probe 12 with a predetermined gain, to thereby generate an RF signal which is a received wave signal.

The phasing addition unit 20 receives, as an input, the RF signal amplified in the receiving unit 16, performs phase control on the signal, forms ultrasonic beams directed to one or more convergence points, and generates RF frame data.

The tomographic image construction unit 22 receives, as an input, the RF frame data from the phasing addition unit 20, and performs signal processing, such as gain compensation, log compression, wave detection, contour enhancement, and filter processing, to thereby construct a tomographic image.

The operating unit 44 is composed of a keyboard having various keys, a track ball, etc. Rotating the track ball of the operating unit 44 enables, for example, the control unit 46 to adjust a range of a display area of the tomographic image.

Then, pressing the enter key on the keyboard of the operating unit 44 enables the control unit 46 to confirm the adjusted area. The control unit 46 then transmits location information of the set display area to the image synthesis unit 24. The image synthesis unit 24 causes the image display unit 26 to display the tomographic image based on the display area.

The AC adaptor 40 receives, as an input, AC power and outputs a predetermined amount of electrical power. The AC adaptor 40 has the function of charging the battery 30 and the function of supplying electrical power to the components. When the AC adaptor 40 is connected to the electric outlet, the AC adaptor 40 is electrically connected to the components and the battery 30.

The battery temperature detection unit 32 has a function of detecting the temperature of the battery 30. More specifically, the battery temperature detection unit 32 is adhered to a predetermined object on the surface of the battery 30 and detects the cell temperatures of cells constituting the battery 30. The battery level detection unit 34 has a function of detecting the battery level of the battery 30. More specifically, the battery level detection unit 34 measures the remaining voltage of the battery 30, thereby detecting the battery level of the battery 30. The battery temperature detection unit 32 and the battery level detection unit 34 may be installed in the battery 30.

Figure 3:
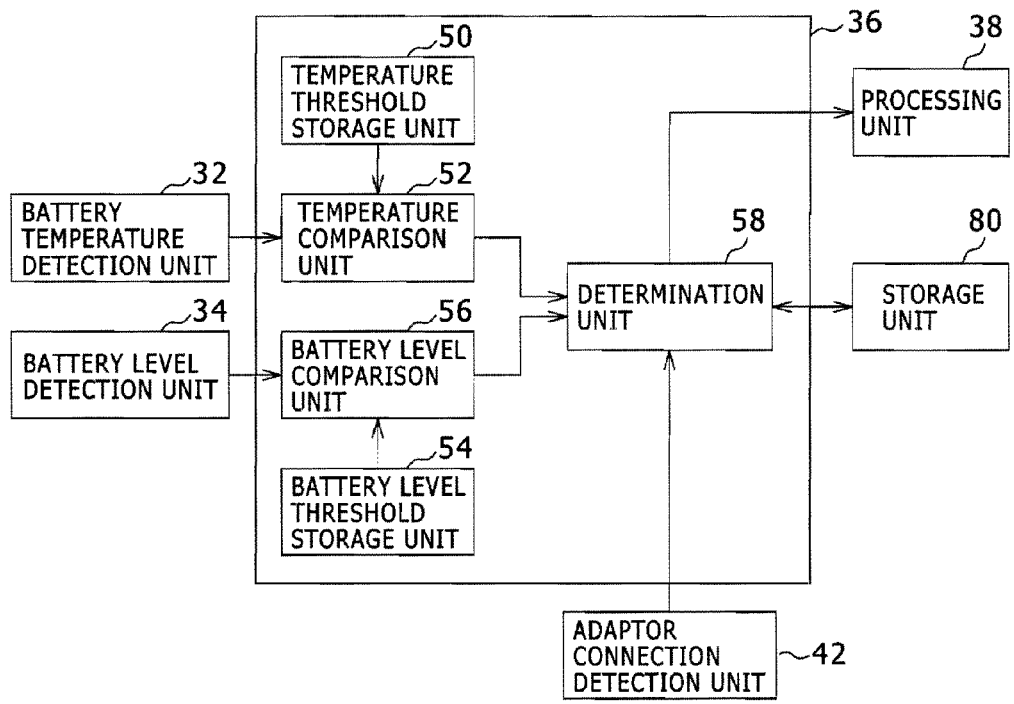
FIG. 3 shows a configuration diagram of a processing determination unit 36 of the present invention.

Next, the processing determination unit 36 will be explained by reference to FIG. 3. The processing determination unit 36 has a temperature threshold storage unit 50 for storing a temperature threshold for the battery 30, a temperature comparison unit 52 for comparing the temperature threshold stored in the temperature threshold storage unit 50 with the temperature of the battery 30 detected by the battery temperature detection unit 32, a battery level threshold storage unit 54 for storing a battery level threshold for the battery 30, a battery level comparison unit 56 for comparing the battery level threshold stored in the battery level threshold storage unit 54 with the battery level of the battery 30 detected by the battery level detection unit 34, and a determination unit 58 for determining a processing method of the processing unit based on the connection state of the AC adaptor 40 detected by the adaptor connection detection unit 42.

Figure 4:
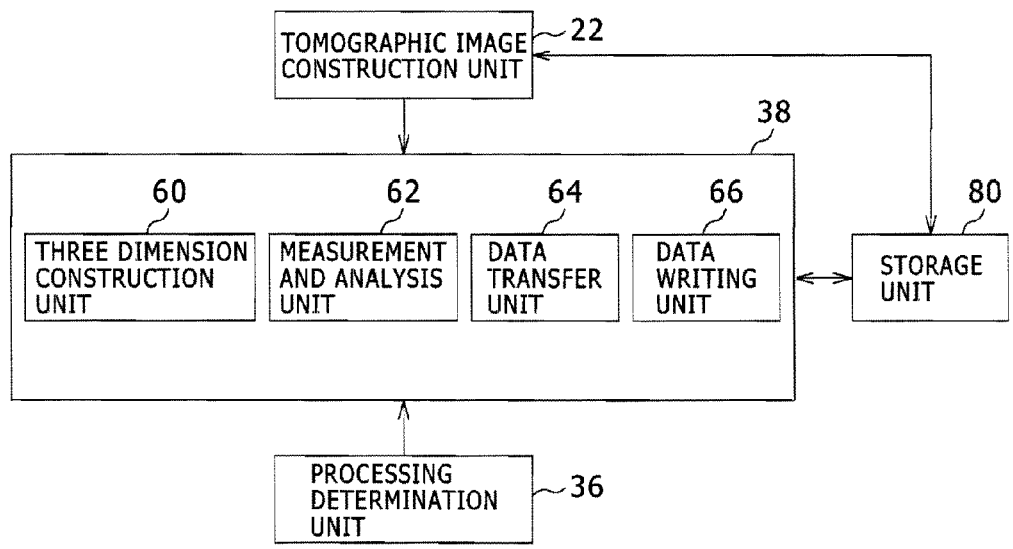
FIG. 4 shows a configuration diagram of a processing unit 38 of the mobile ultrasonic diagnostic device according to the present invention.

The processing unit 38 will be explained by reference to FIG. 4. The processing unit 38 has a component which performs predetermined particular processing. The storage unit 80 stores the predetermined particular processing.

The particular processing is processing which may not be able to be performed when the battery 30 may not be able to supply electrical power. Compared to normal processing performed by the components other than the processing unit 38 (such as, for example, constructing the tomographic image by the tomographic image construction unit 22), the particular processing is time-consuming processing. For example, the particular processing is processing which takes a predetermined processing time (T seconds) or more. T is arbitrary, and may be set by the operating unit 44. The processing determination unit 36 (determination unit 58) can determine the particular processing according to the predetermined time period (T seconds or more) set by the operating unit 44. More specifically, processing which is assumed to take the predetermined time period (T seconds or more) is determined as the particular processing.

The processing unit 38 has at least one of a three-dimensional construction unit 60 for constructing a three-dimensional image based on the tomographic image received from the tomographic image construction unit 22, a measurement and analysis unit 62 for performing measurement by means of, for example, area extraction using the tomographic image received from the tomographic image construction unit 22, a data transfer unit 64 for transferring data based on the tomographic image received from the tomographic image construction unit 22 to outside the mobile ultrasonic diagnostic device, and a data writing unit 66 for writing the data based on the tomographic image received from the tomographic image construction unit 22 into a storage medium. The data based on the tomographic image may be the RF frame data. Further, the storage medium is a medium such as a USB memory or a DVD-RAM.

It is also possible to select, using the operating unit 44, the component to perform the particular processing from among a plurality of processing tasks in the three-dimensional construction unit 60, the measurement and analysis unit 62, the data transfer unit 64, and the data writing unit 66 of the processing unit 38. For example, in order to prevent loss of data being transferred to outside the mobile ultrasonic diagnostic device, the data transfer unit 64 is selected by the operating unit 44. As such, the processing determination unit 36 (determination unit 58) can determine data transfer as the particular processing.

Figure 5:
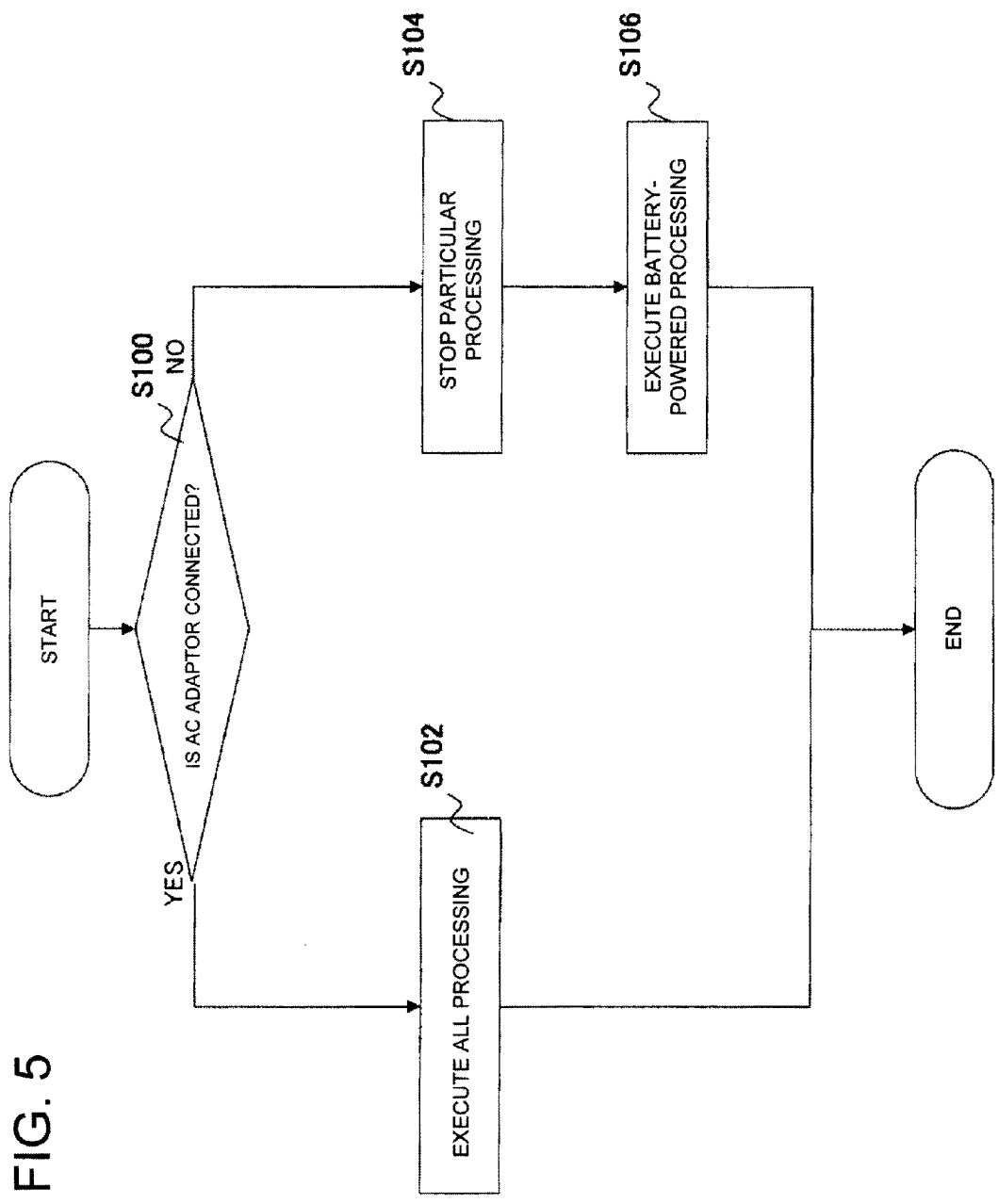
FIG. 5 shows a flowchart illustrating the operation in Embodiment 1 of the present invention.

Next, the operation of the present embodiment in the mobile ultrasonic diagnostic device will be explained by reference to FIG. 5.

(S100)

First, the adaptor connection detection unit 42 detects the connection state of the AC adaptor 40. More specifically, the adaptor connection detection unit 42 detects whether or not the AC adaptor 40 is connected to the electric outlet, based on electrical power supplied from the AC adaptor 40 to the components.

(S102)

If the AC adaptor 40 is connected to the electric outlet, and electrical power is supplied to the components, it is understood that the AC adaptor 40 supplies electrical power to the components and charges the battery 30. Therefore, if the AC adaptor 40 is connected to the electric outlet, because there is no possibility that the battery 30 will not be able to supply electrical power, the processing determination unit 36 (determination unit 58) determines to cause the processing unit 38 to perform all processing. Then, the processing unit 38 performs all processing. Similarly, the components other than the processing unit 38 execute all processing.

(S104)

If the AC adaptor 40 is not connected to the electric outlet, and the battery 30 supplies electrical power to the components, there is a possibility that the battery 30 will not be able to supply electrical power, and therefore, the processing determination unit 36 (determination unit 58) determines to cause the processing unit 38 to stop execution of the predetermined particular processing. The processing unit 38 stops execution of the particular processing. The storage unit 80 stores the particular processing which has been stopped.

When stopping execution of the particular processing, the processing unit 38 stops execution of the particular processing so as not to lose the data being executed in the particular processing. More specifically, after the particular processing is completed in the processing unit 38, the particular processing is stopped. If the particular processing is being executed in the processing unit 38, data relating to the particular processing are stored in the storage unit 80, and after the data has been stored in the storage unit 80, the processing unit 38 stops the particular processing.

For example, if the data transfer unit 64 is transferring the data, the data being transferred are temporarily copied into the storage unit 80. Then, after the data being transferred have been copied into the storage unit 80, the data transfer unit 64 stops transferring the data. Thus, no data are lost while they are being transferred. Further, when the data transfer unit 64 transfers a plurality of packages (groups) of data, it completes transferring the data per package and then stops transferring the data. Therefore, no data are lost while they are being transferred per package. The package is a certain piece of data which is composed of a plurality of pieces of data. That is, a package means a data group composed of a plurality of pieces of data.

Similarly, when the data writing unit 66 is writing data into the storage medium, such as a USB memory or a DVD-RAM, the data being written are temporarily copied into the storage unit 80. Then, after the data being written have been copied into the storage unit 80, the data writing unit 66 stops writing the data. Accordingly, no data are lost while they are being written. Further, when the data writing unit 66 writes a plurality of packages of data, it completes writing data per package, and then stops writing data. Therefore, no data are lost while they are being written per package.

When measurement data or image data obtained by the measurement and analysis unit 62 are deleted, the measurement data or the image data to be deleted are completely deleted. More specifically, when a certain piece of data stored in the storage unit 80 is deleted, that piece of data is completely deleted, and then, the data deletion is stopped.

Further, when measurement data or image data obtained by the measurement and analysis unit 62 are deleted on a per package basis, the measurement data or the image data are completely deleted per package. More specifically, when a certain piece of data stored in the storage unit 80 is deleted per package, all the other pieces of data included in the package to which that piece of data belongs are also deleted. Then, after the data are deleted per package, the data deletion is stopped. That is, as a plurality of pieces of data are deleted on a per package basis, there are no remaining data pieces to be deleted in the package.

If the processing unit 38 interrupts the particular processing, it is possible to cause the image display unit 26 to display items of the interrupted particular processing and inform the operator that the particular processing has been interrupted. The operator can recognize that the particular processing was interrupted before completion.

In summary, if the AC adaptor 40 is not connected to the electric outlet, the processing determination unit 36 (determination unit 58) determines to cause the processing unit 38 to stop execution of the particular processing, and the processing unit 38 stops execution of the particular processing safely.

(S106)

If the AC adaptor 40 is not connected to the electric outlet, the processing determination unit 36 (determination unit 58) determines the components other than the processing unit 38 to execute battery-powered processing. The components other than the processing unit 38 execute the battery-powered processing. The battery-powered processing is processing other than the particular processing, and takes less time than the particular processing. For example, the battery-powered processing includes normal processing, such as constructing the tomographic image by the tomography constructing unit 22.

In other words, if the AC adaptor 40 is not connected to the electric outlet, the processing determination unit 36 (determination unit 58) determines to cause the components other than the processing unit 38 to execute the processing other than the particular processing, and the components other than the processing unit 38 execute the processing other than the particular processing.

Figure 6:
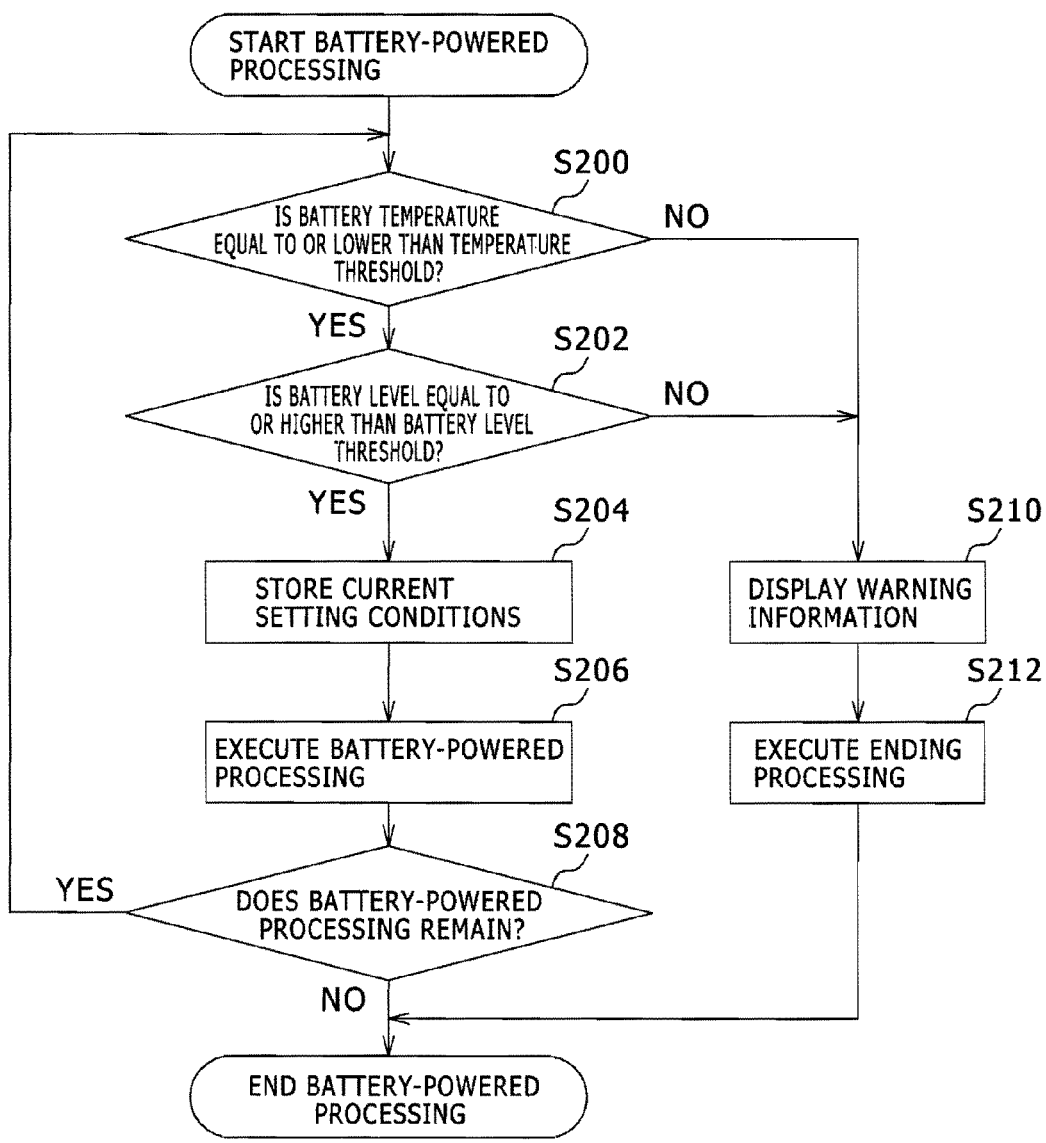
FIG. 6 shows a flowchart illustrating the operation of battery-powered processing according to the present invention.

Next, the operation of the battery-powered processing in S106 will be explained by reference to FIG. 6.

(S200)

The temperature comparison unit 52 compares the temperature threshold stored in the temperature threshold storage unit 50 with the temperature of the battery 30 detected by the battery temperature detection unit 32, and if the temperature of the battery 30 is lower than the temperature threshold, the processing determination unit 36 (determination unit 58) determines that the battery 30 is in a normal state, and that the battery-powered processing is possible. Then, the procedure proceeds to S202. Conversely, if the temperature of the battery 30 is higher than the temperature threshold, the processing determination unit 36 (determination unit 58) determines that the battery 30 is in an abnormal state, and that the battery-powered processing is impossible. Then, the procedure proceeds to S210.

The temperature threshold is set based on a temperature which accelerates deterioration of the battery 30. The temperature threshold can be set as desired via the operating unit 44 and stored in the temperature threshold storage unit 50. For example, the temperature threshold may be set at 50 degrees Celsius.

The battery temperature detection unit 32 detects the temperature of the battery 30 at predetermined time intervals.

The predetermined time interval is an interval of several seconds, such as five seconds. Whenever the battery temperature detection unit 32 detects the temperature of the battery 30 at the predetermined time intervals, the temperature comparison unit 52 compares, at the predetermined time intervals, the temperature threshold stored in the temperature threshold storage unit 50 with the temperature of the battery 30 detected by the battery temperature detection unit 32.

(S202)

The battery level comparison unit 56 compares the battery level threshold stored in the battery level threshold storage unit 54 with the battery level of the battery 30 detected by the battery level detection unit 34, and if the battery level of the battery 30 is higher than the battery level threshold, the processing determination unit 36 (determination unit 58) determines that the battery 30 is in the normal state, and that the battery-powered processing is possible. Then, the procedure proceeds to S204. Conversely, if the battery level of the battery 30 is lower than the battery level threshold, the processing determination unit 36 (determination unit 58) determines that the battery 30 is in then abnormal state, and that the battery-powered processing is impossible. Then, the procedure proceeds to S210.

The battery level threshold is set based on the battery level of the battery 30 at which the battery-powered processing is possible. The battery level of the battery 30 at which the battery-powered processing is possible is a battery level at which the processing which takes less time than the particular processing can be performed. The battery level threshold can be set as desired via the operating unit 44 and stored in the battery level threshold storage unit 54. For example, the battery level threshold can be set at 10 percent.

The battery level detection unit 34 detects the battery level of the battery 30 at the same time intervals as the predetermined time intervals to detect the temperature of the battery 30. Whenever the battery level detection unit 34 detects the battery level of the battery 30 at the predetermined time intervals, the battery level comparison unit 56 compares, at the predetermined time intervals, the battery level threshold stored in the battery level threshold storage unit 54 with the battery level of the battery 30 detected by the battery level detection unit 34.

In other words, the temperature comparison unit 52 and the battery level comparison unit 56 compare the temperature and the battery level of the battery 30 at the same predetermined time intervals. Simultaneously, the battery level comparison unit 56 determines the state of the battery 30 at those predetermined time intervals. Accordingly, the state of the battery 30 can be determined using parameters of the battery 30 without omission.

(S204)

The storage unit 80 stores the current setting conditions of the processing unit 38. The storage unit 80 also stores the particular processing which has been stopped in S104. For example, if transfer of data to outside the mobile ultrasonic diagnostic device has been stopped in S104, the storage unit stores the fact that the data transfer unit 64 was transferring the data.

(S206)

The components other than the processing unit 38 execute the battery-powered processing. The components other than the processing unit 38 execute the processing other than the particular processing. Because the battery-powered processing takes less time than the particular processing, it is completed within a relatively short time period (T seconds or shorter).

The processing determination unit 36 (determination unit 58) determines to cause the components other than the processing unit 38 to execute the battery-powered processing and, if the battery-powered processing is being executed, causes the image display unit 26 to display information of the battery-powered processing, which is the processing other than the particular processing.

Figure 7:
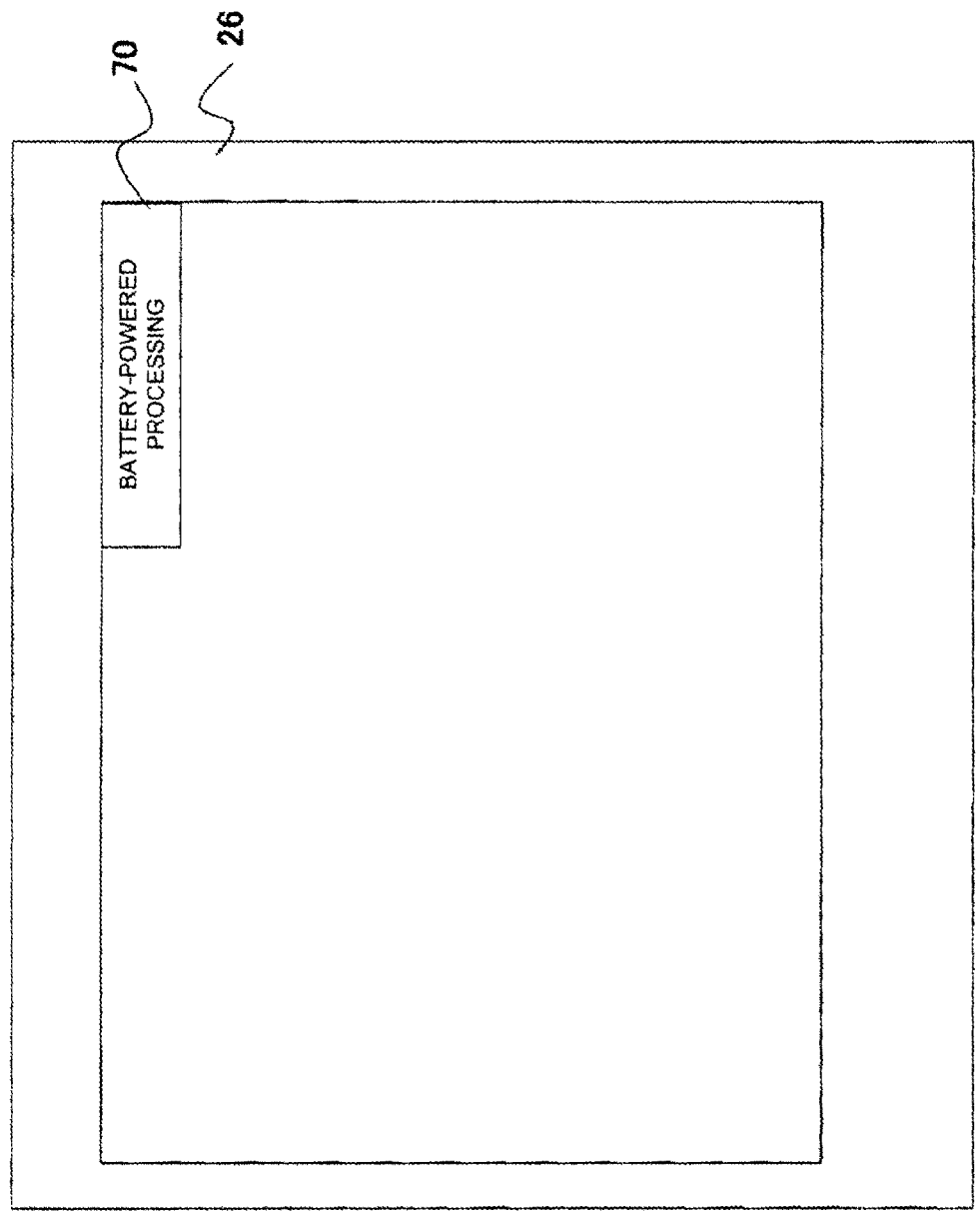
FIG. 7 shows one of display modes of the mobile ultrasonic diagnostic device according to the present invention.

More specifically, as shown in FIG. 7, the image display unit 26 displays a mark 70 indicating that the battery-powered processing, which is the processing other than the particular processing, is being executed. Thus, the operator can recognize that the battery-powered processing is being executed, and that there is a possibility that the battery 30 will not be able to supply electrical power.

(S208)

If there are a plurality of processing tasks other than the particular processing, the processing determination unit (determination unit 58) determines whether or not the battery-powered processing remains. If the battery-powered processing remains, the procedure proceeds to S200. Then, the battery-powered processing continues as long as the temperature and the battery level of the battery 30 satisfy the conditions in S200 and S202, respectively. If the remaining battery-powered processing is too small to satisfy the conditions in S200 and S202, the battery-powered processing ends. Then, ending processing of the mobile ultrasonic diagnostic device can be performed.

(S210)

There is a warning information creation unit (not shown) which creates warning information based on the determination result by the processing determination unit 36 (determination unit 58). The warning information creation unit causes the image display unit 26 to display a message that the battery level of the battery 30 is insufficient, or that the battery-powered processing cannot be performed, and causes the image display unit 26 to display a message prompting to charge the battery 30.

If, from the determination result by the processing determination unit 36 (determination unit 58), the temperature of the battery 30 is found to be higher than the temperature threshold, or if the battery level of the battery 30 is found to be lower than the battery level threshold, the image synthesis unit 24 can freeze the tomographic image displayed on the image display unit 26. In addition, if, from the determination result by the processing determination unit 36 (determination unit 58), the temperature of the battery 30 is found to be higher than the temperature threshold, or if the battery level of the battery 30 is found to be lower than the battery level threshold, the ultrasound transmission and reception control unit 18 can be controlled so as not to receive ultrasonic waves.

In other words, the mobile ultrasonic diagnostic device can be switched to a power-saving mode based on the determination result by the processing determination unit 36 (determination unit 58). Therefore, the operation time of the mobile ultrasonic diagnostic device can be prolonged.

(S212)

The ending processing of the mobile ultrasonic diagnostic device is executed. The ending processing is processing to automatically shut down the mobile ultrasonic diagnostic device safely, even if there is processing being executed. This processing will be described in detail below. Then, the ending processing of the mobile ultrasonic diagnostic device is executed, and the battery-powered processing ends.

Figure 8:
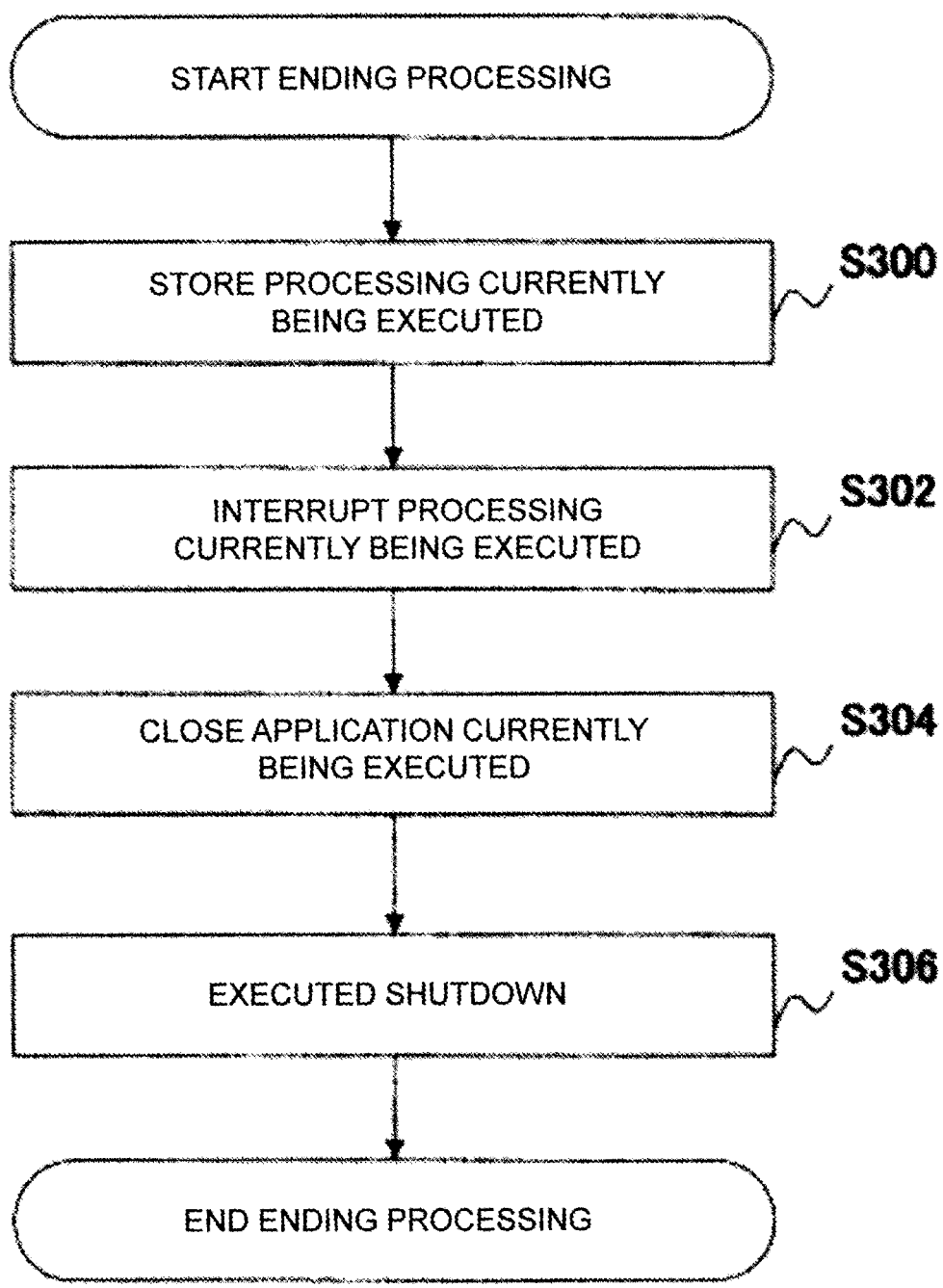
FIG. 8 shows a flowchart illustrating the operation of ending processing according to the present invention.

Next, the operation of the ending processing of the mobile ultrasonic diagnostic device in S212 will be explained below by reference to FIG. 8.

(S300)

The storage unit 80 stores the processing being executed in the component other than the processing unit 38 as the stopped battery-powered processing. If there are a plurality of processing tasks other than the particular processing, the storage unit 80 stores each of the processing tasks as the battery-powered processing.

(S302) (S304)

The component other than the processing unit 38 interrupts the processing being executed and closes the application. If there are a plurality of processing tasks other than the particular processing, the components other than the processing unit 38 interrupt the processing tasks and close the applications.

(S306)

After the processing tasks being executed are interrupted, and the applications are closed, shutdown of the mobile ultrasonic diagnostic device is executed. The ending processing of the mobile ultrasonic diagnostic device is completed. As such, even if there are processing tasks being executed, the mobile ultrasonic diagnostic device can be automatically shut down safely.

As described above, the present invention has the battery 30, the adaptor connection detection unit 42 which detects a connection state of the AC adaptor 40 for supplying electrical power to the components, and the processing determination unit 36 (determination unit 58) which determines the processing in the components based on the connection state of the AC adaptor 40, and the present invention performs the processing in the components (the processing unit 38 and the components other than the processing unit 38) based on the processing determined by the processing determination unit 36 (determination unit 58). Therefore, even if there is a possibility that the battery 30 will not be able to supply electrical power, the mobile ultrasonic diagnostic device can be used safely.

Embodiment 2

Figure 9:
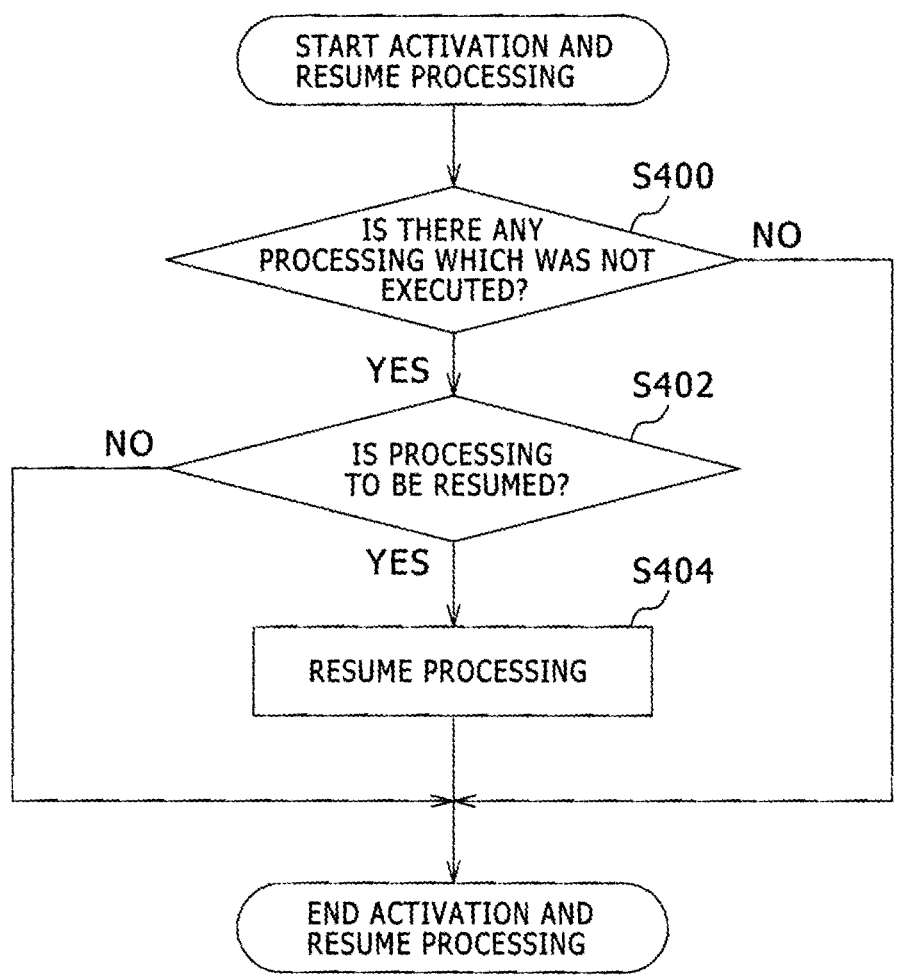
FIG. 9 shows a flowchart illustrating activation and resume processing according to the present invention.

Next, Embodiment 2 will be explained by reference to FIG. 9. Embodiment 2 differs from Embodiment 1 in that the processing which was not executed before the ending processing of the mobile ultrasonic diagnostic device is resumed at the time of startup.

(S400)

The storage unit 80 stores the particular processing which was stopped in S104. The storage unit 80 also stores the battery-powered processing which was stopped in S300. That is, the storage unit 80 stores the processing which was not executed. The processing which was not executed is read out from the storage unit 80 and displayed on the image display unit 26. The operator can recognize the processing which was not executed.

If there is any processing which was not executed, the procedure proceeds to S402. If there is no processing which was not executed, the activation and resume processing ends.

(S402)

The operator selects whether or not to resume the processing which was not executed via the operating unit 44. If the operator wishes to execute the particular processing in the processing unit 38, it is necessary for the AC adaptor 40 to be connected to the electric outlet, to thereby supply electrical power to the components. When the operator connects the AC adaptor 40 to the electric outlet, the processing unit 38 can resume the particular processing.

If the operator wishes to execute the battery-powered processing in the components other than the processing unit 38, it is necessary for the AC adaptor 40 to be connected to the electric outlet, to thereby supply electrical power to the components, or it is necessary for the conditions of S200 and S202 to be satisfied. When the operator connects the AC adaptor to the electric outlet or charges the battery 30, the components other than the processing unit 38 can resume the battery-powered processing.

(S404)

The particular processing stopped in the processing unit 38 in S104 is resumed. If, for example, data transfer by the data transfer unit 64 was stopped in S104, upon restart of data transfer which was stopped, information of the stopped particular processing (data transfer) and the data which were copied during transfer are read out from the storage unit 80. The data transfer unit 64 then transfers the data. If data transfer for a plurality of packages was stopped in the data transfer unit 64, the data which were copied per package during transfer are read out from the storage unit 80. The data transfer unit 64 then transfers the data per package.

Similarly, if data writing was stopped in the data writing unit 66, information of the stopped particular processing (data writing) and the data which were copied during writing processing are read out from the storage unit 80. The data writing unit 66 then resumes writing the data into the recording medium, such as a USB memory and a DVD-RAM. If data writing for a plurality of packages is stopped in the data writing unit 66, the data which were copied per package during data writing are read out from the storage unit 80. The data writing unit 66 resumes writing the data into the recording medium, such as a USB memory or a DVD-RAM, per package.

In addition, if deletion of measured data or image data by the measurement and analysis unit 62 was stopped, or if deletion of the data stored in the storage unit 80 was stopped, that stopped data deletion is resumed.

Further, if the processing unit 38 resumes the particular processing, it is possible to cause the image display unit 26 to display an item of the particular processing which has been resumed, and inform the operator that the particular processing has been resumed. The operator can recognize that the interrupted particular processing has been resumed.

Still further, in S300, the battery-powered processing which has been stopped in the component other than the processing unit 38 is resumed.

As such, the present embodiment has the storage unit for storing the processing which was not executed during the processing in the components, and resumes, at the time of startup of the device, the processing which was not executed. Accordingly, it is possible to resume, at the time of startup, the processing which was not executed until the ending processing of the mobile ultrasonic diagnostic device.

REFERENCE NUMERALS

2 BODY CHASSIS, 4 KEYBOARD CHASSIS, 6 DISPLAY CHASSIS, 8 CABLE, 10 TEST OBJECT, 12 ULTRASOUND PROBE, 14 TRANSMITTING UNIT, 16 RECEIVING UNIT, 18 ULTRASOUND TRANSMISSION AND RECEPTION CONTROL UNIT, 20 PHASING ADDITION UNIT, 22 TOMOGRAPHIC IMAGE CONSTRUCTION UNIT, 24 IMAGE SYNTHESIS UNIT, 26 IMAGE DISPLAY UNIT, 30 BATTERY, 32 BATTERY TEMPERATURE DETECTION UNIT, 34 BATTERY LEVEL DETECTION UNIT, 36 PROCESSING DETERMINATION UNIT, PROCESSING UNIT, 40 AC ADAPTOR, 42 ADAPTOR CONNECTION DETECTION UNIT, 44 OPERATING UNIT, 46 CONTROL UNIT.

The invention claimed is:

1. A mobile ultrasonic diagnostic device comprising:
   a battery;
   an adaptor connection detection unit which detects a connection state of an AC adaptor which supplies electrical power;
   an ultrasound probe;
   a tomographic image construction unit which constructs a tomographic image based on RF frame data related to ultrasonic beams transmitted from and received by the ultrasound probe;
   a data transfer unit which transfers data based on the tomographic image constructed by the tomographic image construction unit; and
   a processing determination unit which determines processing for at least one of the tomographic image construction unit and the data transfer unit to stop when the adaptor connection detection unit detects the connection state of the AC adaptor to be disconnected.

2. The mobile ultrasonic diagnostic device according to claim 1, further comprising a storage unit, wherein when the data is being transferred by the data transfer unit and the processing determination unit determines processing for the data transfer unit to stop, the data being transferred is temporarily copied into the storage unit, and after the data being transferred is copied in the storage unit, the data transfer unit stops transferring the data.

3. The mobile ultrasonic diagnostic device according to claim 2, wherein when the data transfer unit stopped transferring the data and resumes data transfer which was stopped, information of data transfer which was stopped and the data which was copied during data transfer are read out from the storage unit, and the data transfer unit transfers the data.

4. A mobile ultrasonic diagnostic device comprising:
   a battery;
   an adaptor connection detection unit which detects a connection state of an AC adaptor which supplies electrical power;
   an ultrasound probe;
   a tomographic image construction unit which constructs a tomographic image based on RF frame data related to ultrasonic beams transmitted from and received by the ultrasound probe;
   a data writing unit which writes the data based on the tomographic image constructed by the tomographic image construction unit to an external storage medium; and
   a processing determination unit which determines processing for at least one of the tomographic image construction unit and the data writing unit to stop when the adaptor connection detection unit detects the connection state of the AC adaptor to be disconnected.

5. The mobile ultrasonic diagnostic device according to claim 4, further comprising a storage unit, wherein when the data is being written by the data writing unit to the external storage medium and the processing determination unit determines the data writing unit to stop, the data being written is temporarily copied into the storage unit, and after the data being written is copied in the storage unit, the data writing unit stops writing the data to the external storage medium.

6. The mobile ultrasonic diagnostic device according to claim 5, wherein when the data writing unit stopped writing the data and resumes data writing which was stopped, information of data writing which was stopped and the data which was copied during data writing are read out from the storage unit, and the data writing unit resumes the data writing to the external storage medium.

* * * * *